United States Patent

Motoyama et al.

[11] Patent Number: 5,756,816
[45] Date of Patent: May 26, 1998

[54] PROCESS FOR THE PRODUCTION OF PHENOL DERIVATIVES

[75] Inventors: Yuki Motoyama; Tomoyuki Yui, both of Tsukuba, Japan

[73] Assignee: Mitsubishi Gas Chemical Company, Inc., Tokyo, Japan

[21] Appl. No.: 788,465

[22] Filed: Jan. 29, 1997

[30] Foreign Application Priority Data

Feb. 1, 1996 [JP] Japan ................................ 8-016550

[51] Int. Cl.$^6$ ................................................. C07C 96/78
[52] U.S. Cl. ................................................. 560/112; 560/111
[58] Field of Search ................................... 560/111, 112

[56] References Cited

FOREIGN PATENT DOCUMENTS

| | | |
|---|---|---|
| 0 355480 | 2/1990 | European Pat. Off. . |
| 0 362714A | 4/1990 | European Pat. Off. . |
| A-4-82862 | 3/1992 | Japan . |
| A-4-234841 | 8/1992 | Japan . |

OTHER PUBLICATIONS

"Protective Groups in Organic Synthesis" Greene 1991 pg. 88–90 Pub. John Wiley & Sons.
"Advanced Organic Chemistry" Jerry March 1968 338–339.
CA 119:282389–AB578F JP 05163208 Jun. 29, 1993 Iwane, Prep. of Biphenyl Carboxylates.
Manuals for Organic Chemical Experiments, Synthesis Reactions II, 15, pp. 14–15.

*Primary Examiner*—C. Warren Ivy
*Assistant Examiner*—Jean F Vollano
*Attorney, Agent, or Firm*—Sherman and Shalloway

[57] ABSTRACT

A process for the production of a phenol derivative of the formula (2), which comprises subjecting a diester compound of the formula (1) in which a hydroxyl group is protected by an acyl group, to a reaction for removal of protection, wherein the reaction is carried out in the presence of an aliphatic amine as a protection-removal agent,

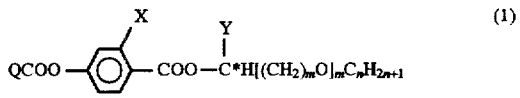

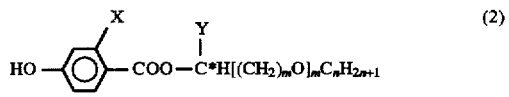

wherein X is hydrogen or fluorine, Y is —$CH_3$ or —$CF_3$, Q is an alkyl group having 1 to 4 carbon atoms, p is 0 or 1, m is an integer of 2 to 7, n is an integer of at least 1, and C* is an asymmetric carbon, the process enabling to obtain the phenol derivative of the formula (2) useful as an intermediate for a liquid crystal compound with ease and at high purity.

14 Claims, No Drawings

PROCESS FOR THE PRODUCTION OF PHENOL DERIVATIVES

TECHNICAL FIELD OF THE INVENTION

The present invention relates to a process for the production of phenol derivatives. More specifically, it relates to a process for the production of optically active phenol derivatives useful as an intermediate for a liquid crystal compound by removing the protection of a phenol derivative protected by an acyl group.

PRIOR ART

Liquid crystal compounds having a variety of structures, including a nematic liquid crystal compound, are known. Of these known compounds, the nematic liquid crystal compound is remarkably promising for use in a liquid crystal display for which the electro-optical properties thereof are adapted. Further, ferroelectric liquid crystal compounds and anti-ferroelectric liquid crystal compounds have been developed in recent years, and studies have been and are vigorously made to put them to practical use. These liquid crystal compounds have been rapidly increasing in kind.

In the fields of ferroelectric liquid crystal compounds and anti-ferroelectric liquid crystal compounds, liquid crystal compounds having a variety of structures have come to be known, while most of the liquid crystal compounds have a structure of R—O—Ph—Ph—COO—Ph—COO—R* (wherein R is a linear alkyl, Ph is 1,4-phenylene and R* is an optically active group), and these compounds are the most essential.

As a general method of producing the liquid crystal compound having the above structure, a reaction scheme of the following (1) to (5) is known.

| | |
|---|---|
| (1) R'—O—Ph(X)—COOH + SOCl$_2$ | → R'—O—Ph(X)—COCl |
| (2) R'—O—Ph(X)—COCl + R*OH | → R'—O—Ph(X)—COO—R* |
| (3) R'—O—Ph(X)—COOR* | → HO—Ph(X)—COO—R* |
| (4) R—O—Ph—Ph—COOH + SOCl$_2$ | → R—O—Ph—Ph—COCl |
| (5) R—O—Ph—Ph—COCl + HO—Ph—COO—R* | → R—O—Ph—Ph—COO—Ph(X)—COO—R* |

In the above reaction scheme, R' is a protective group for a hydroxyl group, R is linear alkyl, Ph is 1,4-phenylene, Ph(X) is 1,4-phenylene optionally substituted with fluorine (X), and R*OH is an optically active alcohol.

The above reaction scheme is outlined as follows.

(1) Chlorination of benzoic acid in which a hydroxyl group on the p-position is protected by a proper protective group.
(2) Formation of an ester by a reaction between chlorinated benzoic acid chloride and an optically active alcohol.
(3) Formation of a phenol derivative by a reaction for removal of the protection.
(4) Chlorination of 4'-alkyloxybiphenyl-4-carboxylic acid.
(5) Formation of a liquid crystal compound by a reaction between a product formed in (3) and a product formed in (4).

In a series of the above reactions, the protective group (R') for the hydroxyl group in (1) is generally benzyl (C$_6$H$_5$—CH$_2$—) (e.g., see JP-A-4-234841) or acetyl (e.g., see JP-A-4-82862).

Further, the reaction in which the protection is removed in (3) is conventionally carried out as follows.

That is, when the protective group (R') is benzyl, the protection is removed by hydrogenation in the presence of a Pd/carbon catalyst to convert the benzyl group to toluene. When the protective group (R') is acetyl, generally, there is known a method in which hydrolysis is carried out in the presence of a strong alkali such as sodium hydroxide or potassium hydroxide ("Yuukikagaku Jikken no Tebiki (Manuals for Organic Chemical Experiments) - Synthesis Reactions II, 15", published by Kagaku Dojin) or a method in which hydrolysis is carried out in mixed solvents of methanol, tetrahydrofuran and water in the presence of lithium hydroxide (see JP-A-4-234841).

Under the above conditions, however, the hydrolysis of an ester on the optically active side undesirably simultaneously takes place. Generally, therefore, benzylamine (JP-A-4-82862) is used as a protection-removal agent for such a compound of the formula (1).

As described above, benzyl and acetyl are generally used as a protective group (R') for a hydroxyl group.

The protection by benzyl is easily removed by hydrogenation in the presence of a Pd/carbon catalyst. This removal of the protection can be applied to compounds having the structure of C$_6$H$_5$—CH$_2$—O—Ph—COO—R* (in which Ph is 1,4-phenylene) without any problem, but it causes a problem on the removal of protection in the following compound (A1) substituted with fluorine on a benzene ring.

That is, when the protection is removed by hydrogenation, the carbon-hydrogen bond of the benzene ring is broken, and benzyl is substituted to form the following compound (A2) as a byproduct.

The byproduct (A2) is difficult to separate and works as a factor to deteriorate the chemical purity of a liquid crystal as an end product. The chemical purity of a liquid crystal is one of the factors which determine the characteristics of the liquid crystal, and hence, the formation of such byproduct difficult to separate is undesirable.

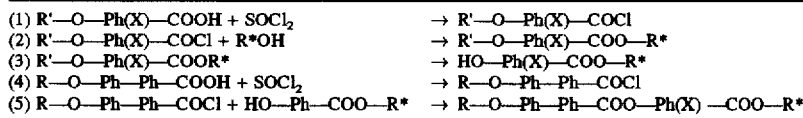

A$_1$

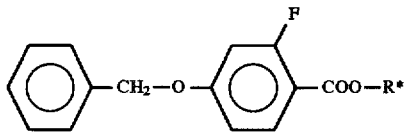

A$_2$

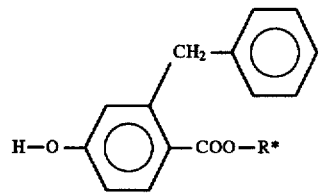

On the other hand, in the removal of the protection by acetyl, generally, a benzyl amine which admits a reaction for the removal of protection in a non-aqueous solvent is used as a protection-removal agent, for preventing the hydrolysis of an ester on the optically active side (R*).

When benzylamine is used as a protection-removal agent, benzylacetamide is formed as a product. This product is naturally formed in an equimolar amount to the end product, but it cannot be separated by usual means. Therefore, special separation means such as column chromatography is required. However, in the separation from the end product by column chromatography, no proper solvent is available for readily eluting the benzylacetamide, and the benzylacetamide remains in the column, which results in an extremely decreased life of a column packing and causes a problem on the cost performance of a separation and purification means.

The above explanations can be summarized as follows. Benzyl is not proper as a protective group, since there is an essential problem caused by a side reaction during the removal of protection. Acetyl can be therefore said to be proper. When the protective group is acetyl, benzylamine has been used as a proper protection-removal agent. Since, however, it is difficult to separate formed benzylacetamide from the end product so that the benzylamide overloads a column chromatography as separation means, acetyl cannot be said to be preferred in view of economic performance.

It is an object of the present invention to provide a process for the production of a phenol derivative, which process causes no decomposition of an ester on the optically active side (R*), permits the easy removal of acetyl as a protective group, and permits the easy separation of a product formed due to the protective group generated by the removal of protection from the system.

According to studies of the present inventors, the above object is achieved by a process for the production of a phenol derivative of the following formula (2), which comprises subjecting a diester compound of the following formula (1) in which a hydroxyl group is protected by an acyl group, to a reaction for removal of protection, wherein the reaction is carried out in the presence of an aliphatic amine as a protection-removal agent.

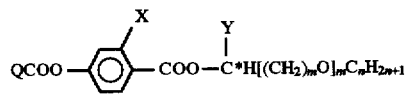
(1)

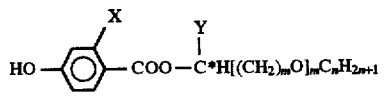
(2)

wherein X is hydrogen or fluorine, preferably fluorine, Y is —CH$_3$ or —CF$_3$, Q is an alkyl group having 1 to 4 carbon atoms, preferably —CH$_3$, p is 0 or 1, m is an integer of 2 to 7, n is an integer of at least 1, preferably 1 to 10, and C* is an asymmetric carbon.

In the present invention, the aliphatic amine as a protection-removal agent is preferably a primary linear alkylamine, and it is more preferably methylamine, ethylamine or n-propylamine in view of easiness (water solubility) for the removal of acetamides formed as a byproduct in the reaction. Further, methylamine is particularly effective in view of a reaction rate. The amount of the aliphatic amine per mole of the diester compound of the formula (1) is properly 1.5 to 2.5 moles.

The reaction temperature for the removal of protection is preferably as low as possible, since the ester decomposition may take place on the optically active side (R*). When the above reaction temperature is too low, however, the intended reaction may not proceed. The above temperature is therefore preferably in the range of from 20° to 35° C.

The solvent used in the reaction in the present invention is selected from methanol, water or a mixture of these. Methanol is particularly preferred for preventing the hydrolysis of ester on the optically active side and obtaining a uniform reaction system.

Alkylacetamides derived from the protective group, formed by the reaction in the present invention, are very easily soluble in water, and they therefore can be simply removed from the reaction system by washing the reaction mixture with water.

In the present invention, the removal of protection (deacylation) of a diester compound protected by an acyl group is carried out in the presence of the aliphatic amine, and formed alkylacetamides can be therefore easily removed from the reaction system by washing the reaction mixture with water, whereby it is made possible to produce an intermediate of a liquid crystal, having a very high chemical purity.

EXAMPLES

The present invention will be more specifically explained with reference to Examples and Comparative Examples hereinafter, while the present invention shall not be limited thereto.

EXAMPLE 1

A reactor was charged with 1 g of 4-acetoxy-2-fluoro-1-(6-ethoxy-1-trifluoromethylhexyloxy-carbonyl)benzene (formula (1); X=F, Y=—CF$_3$, Q=—CH$_3$, m=1, p=5, n=2), 15 ml of toluene and 0.5 g of a methanol solution containing 40 wt% methylamine, and the mixture is stirred at room temperature for 15 minutes. After the reaction, the reaction mixture was washed with a 4 wt% hydrochloric acid aqueous solution and then with water to separate an organic layer from the solution. The organic layer was dried over anhydrous sodium sulfate, and then, the solvent is distilled off to give 4-hydroxy-2-fluoro-1-(6-ethoxy-1-trifluoromethylhexyloxy-carbonyl)benzene (formula (2); X=F, m=1, p=5, n=2). This product was dissolved in acetone and analyzed by gas chromatography to show no presence of methylacetamide (CH$_3$CONHCH$_3$).

EXAMPLE 2

A reactor was charged with 1 g of 4-acetoxy-1-(1-methylheptyloxycarbonyl)benzene (formula (1); X=H, m=0, n=6), 15 ml of toluene and 0.55 g of a methanol solution containing 40 wt% methylamine, and the mixture is stirred at room temperature for 3 hours. After the reaction, the reaction mixture was washed with a 4 wt % hydrochloric acid aqueous solution and then with water to separate an organic layer from the solution. The organic layer was dried over anhydrous sodium sulfate, and then, the solvent is distilled off to give 4-hydroxy-1-(1-methylheptyloxycarbonyl)benzene (formula (2); X=H, m=0, n=6). This product was dissolved in acetone and analyzed by gas chromatography to show no presence of methylacetamide (CH$_3$CONHCH$_3$).

REFERENTIAL EXAMPLE 1

Example 1 was repeated except that the reaction temperature was changed to 10° C. The product obtained after a reaction time of 3 hours was analyzed by gas chromatography to show that about 10% of 4-acetoxy-2-fluoro-1-(6-ethoxy-1-trifluoromethylhexyloxycarbonyl)benzene remained. It appeared that the reaction temperature of 10° C. required a longer reaction time for completing the reaction.

EXAMPLES 3–5

The reaction in Example 1 was repeated except that the methylamine was replaced with ethylamine (70% aqueous solution), n-propylamine or iso-propylamine. The time required for completing the reaction and the water solubility of acetamide formed as a byproduct were studied, and Table 1 shows the results.

The acetamide formed as a byproduct in each Example was excellent in water solubility, while the reaction in each Example took a little longer period of time than the reaction in Example 1.

TABLE 1

| Example No. | Amine | Time required for completing reaction (hr) | Water solubility of acetamide as byproduct |
|---|---|---|---|
| 3 | Ethylamine | 1 | Excellent |
| 4 | N-propylamine | 1 | Excellent |
| 5 | iso-Propylamine | 3 | Excellent |

EXAMPLE 6

Example 1 was repeated except that the 4-acetoxy-2-fluoro-1-(6-ethoxy-1-trifluoromethylhexyloxycarbonyl)-benzene was replaced with 4-propanoyloxy-1-(6-ethoxy-1-trifluoromethylhexyloxycarbonyl)benzene (formula (1); X=H, Y=—CF$_3$, Q=—C$_2$H$_5$, m=1, p=5, n=2). As a result, it was confirmed that the propanoyl group was completely eliminated, and methyl propionic acid amide formed by a reaction between the eliminated propanoyl group and methylamine was shifted to a substantial aqueous phase by post treatment.

COMPARATIVE EXAMPLE 1

A reactor was charged with 1 g of 4-acetoxy-2-fluoro-1-(6-ethoxy-1-trifluoromethylhexyloxycarbonyl)-benzene, 15 ml of ethanol and 0.6 g of benzylamine, and the mixture was stirred at room temperature for 5 hours. After the reaction, the reaction mixture solution was poured into water and subjected to extraction with dichloromethane. An organic layer was consecutively washed with a hydrochloric acid aqueous solution and with water, and dried over anhydrous sodium sulfate. The solvent was removed to give a crude 4-hydroxy-2-fluoro-1-(6-ethoxy-1-trifluoromethylhexyloxycarbonyl)benzene. This product was analyzed by thin film chromatography to show that benzylacetamide was co-present in addition to the end product.

The above crude product was purified by column chromatography using hexane/ethyl acetate (=5/1) as an elution liquid and silica gel as a filler. The intended 4-hydroxy-2-fluoro-1-(6-ethoxy-1-trifluoromethylhexyloxy-carbonyl)benzene had a purity of at least 98% (by liquid chromatography. Elvent: hexane, packing material: silica gel). On the other hand, benzylacetamide as a byproduct was difficult to elute even if the solvent was ethyl acetate alone.

COMPARATIVE EXAMPLE 2

An autoclave was charged with 1 g of 4-benzyloxy-2-fluoro-1-(6-ethoxy-1-trifluoromethylhexyloxycarbonyl)-benzene, 15 ml of ethyl acetate and 0.5 g of a 15 wt % Pd/carbon catalyst, the atmosphere in the autoclave was replaced with nitrogen and then with hydrogen, and the mixture was continuously stirred at room temperature until the hydrogen absorption terminated. After the reaction, the catalyst was filtered off. The ethyl acetate was distilled off to give a crude 4-hydroxy-2-fluoro-1-(6-ethoxy-1-trifluoromethyl-hexyloxycarbonyl)benzene.

A liquid crystal compound, 3-fluoro-4-(6-ethoxy-1-trifluoromethylhexyloxycarbonyl)phenyl-4'-nonyloxybiphenyl-4-carboxylate from the above product by a conventional method.

The above liquid crystal was analyzed by thin film chromatography and liquid chromatography to show the presence of an unknown compound in addition to the end product. The unknown compound was isolated from the end product by column chromatography (elvent: dichloromethane, packing material: silica gel) and measured for NMR spectrum (see Table 2). As a result, the unknown compound was assumed 5 to be a compound having the following structure. It is assumed from the following chemical structure that the above compound was formed when the protection by benzyl was removed by the hydrogenation.

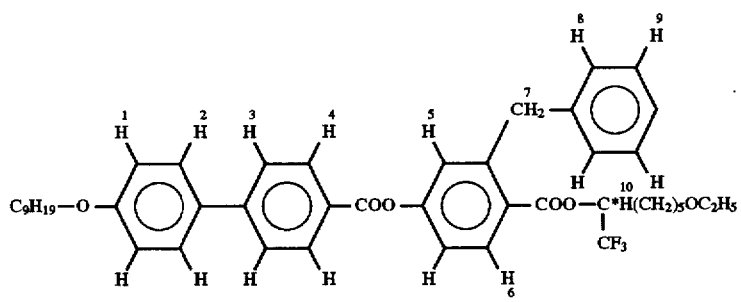

TABLE 2

| Hydrogen atomic number | 1 | 2 | 3 | 4 | 5 | 6 | 7 | 8 9 | 10 |
|---|---|---|---|---|---|---|---|---|---|
| ppm | 7.0 | 7.6 | 7.7 | 8.1 | 7.1 | 7.9 | 4.0 | 7.2–7.4 | 5.6 |

COMPARATIVE EXAMPLES 3–5

The reaction in Example 1 was repeated except that the methylamine was replaced with diethylamine, n-butylamine or tert-butylamine.

The time required for completing the reaction and the water solubility of acetamides formed as a byproduct were studied, and Table 3 shows the results.

In each Comparative Example, the acetamides formed as a byproduct were scarcely soluble in water, and the reaction took a long time.

TABLE 3

| Comparative Example | Amine | Time required for completing reaction (hr) | Water solubility of acetamide as byproduct |
|---|---|---|---|
| 3 | Diethylamine | 7 | Poor |
| 4 | N-Butylamine | 1 | Poor |
| 5 | tert-Butylamine | 24 | Poor |

What is claimed is:

1. A process for the production of a phenol derivative of the formula (2), which comprises subjecting a diester compound of the formula (1) in which a hydroxyl group is protected by an acyl group, to a reaction for removal of protection, wherein the reaction is carried out in the presence of a non-substitute alkylamine as a protection-removal agent,

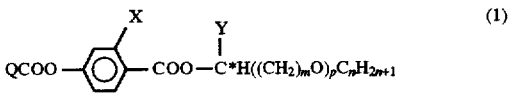

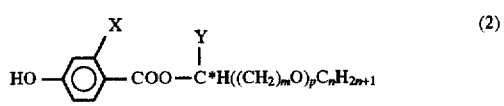

wherein X is hydrogen or fluorine, Y is $-CH_3$ or $-CF_3$, Q is an alkyl group having 1 to 4 carbon atoms, p is 0 or 1, m is an integer of 2 to 7, n is an integer of 1 to 10, and C* is an asymmetric carbon.

2. The process of claim 1, wherein the alkylamine is a member selected from the group consisting of methylamine, ethylamine and n-propylamine.

3. The process of claim 1, wherein the linear alkylamine is methylamine.

4. The process of claim 1, wherein the aliphatic amine is used in an amount of 1.5 to 2.5 moles per mole of the diester compound of the formula (1).

5. The process of claim 1, wherein the reaction for removal of the protection is carried out at a temperature between 20° C. and 35° C.

6. The process of claim 1, wherein the reaction for removal of the protection is carried out in the presence of a solvent comprising methyl alcohol, water or a mixture thereof.

7. The process of claim 1, wherein the reaction for removal of the protection is carried out in the presence of a solvent comprising methyl alcohol.

8. The process of claim 1, wherein Q is an alkyl group having 1 or 2 carbon atoms.

9. A process for the production of a phenol derivative of the formula (2), which comprises subjecting a diester compound of the formula (1) in which a hydroxyl group is protected by an acyl group, to a reaction for removal of protection, wherein the reaction is carried out in the presence of a $C_1$–$C_3$ alkylamine as a protection-removal agent,

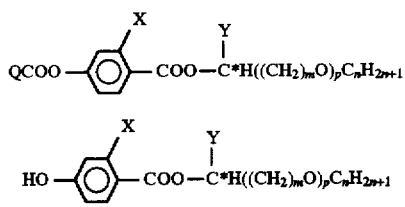

wherein X is hydrogen or fluorine, Y is $-CH_3$ or $-CF_3$, Q is an alkyl group having 1 to 4 carbon atoms, p is 0 or 1, m is an integer of 2 to 7, n is an integer of 1 to 10, and C* is an asymmetric carbon, the aliphatic amine is used in an amount of 1.5 to 2.5 moles per mole of the diester compound of the formula (1) and the reaction for removal of the protection is carried out at a temperature between 20° C. and 35° C. in the presence of a solvent comprising methyl alcohol or water or a mixture thereof.

10. The process of claim 9, wherein the alkylamine is a member selected from the group consisting of methylamine, ethylamine or n-propylamine.

11. The process of claim 9, wherein the alkylamine is methylamine.

12. The process of claim 9, wherein the alkylamine is iso-propylamine.

13. The process of claim 9, wherein the reaction for removal of the protection is carried out in the presence of a solvent comprising methyl alcohol.

14. The process of claim 9, wherein Q is an alkyl group having 1 or 2 carbon atoms.

* * * * *